United States Patent
Blondeel et al.

(10) Patent No.: US 6,415,992 B1
(45) Date of Patent: Jul. 9, 2002

(54) SPRAY DEVICE CONTAINING NITROGEN-CARBON DIOXIDE PROPELLENT GAS MIXTURE

(75) Inventors: Gilles Blondeel, Aulnay S/Bois; Nicole Le Calvez, Villebon S/Yvette, both of (FR)

(73) Assignee: L'Oreal, Clichy (FR)

( * ) Notice: Subject to any disclaimer, the term of this patent is extended or adjusted under 35 U.S.C. 154(b) by 518 days.

(21) Appl. No.: 08/739,836

(22) Filed: Oct. 30, 1996

(30) Foreign Application Priority Data

Oct. 30, 1995 (FR) ............................................. 95 12788

(51) Int. Cl.⁷ ................................................. B05B 7/32
(52) U.S. Cl. ...................... 239/337; 222/394; 222/402.1
(58) Field of Search ............................. 222/394, 402.1; 239/337, 340, 492

(56) References Cited

U.S. PATENT DOCUMENTS

| | | | | |
|---|---|---|---|---|
| 4,203,552 A | * | 5/1980 | Hayes | 239/337 |
| 4,940,171 A | * | 7/1990 | Gilroy | 222/402.1 |
| 5,037,001 A | * | 8/1991 | Presant | 222/402.1 |
| 5,083,685 A | * | 1/1992 | Amemiya et al. | 222/402.1 |
| 5,085,347 A | * | 2/1992 | Hayes et al. | 222/402.1 |
| 5,211,317 A | * | 5/1993 | Diamond et al. | 222/402.1 |
| 5,370,313 A | * | 12/1994 | Beard | 239/337 |
| 5,628,432 A | * | 5/1997 | Mosley | 239/337 |

FOREIGN PATENT DOCUMENTS

| | | |
|---|---|---|
| BR | 7808500 | 4/1979 |
| JP | 2-53886 | 2/1990 |
| JP | 6-340519 | 12/1994 |
| JP | 8-73839 | 3/1996 |

* cited by examiner

*Primary Examiner*—Lesley D. Morris
(74) *Attorney, Agent, or Firm*—Oblon, Spivak, McClelland, Maier & Neustadt, P.C.

(57) ABSTRACT

The invention concerns a new personal spray device pressurized by a gas mixture comprising nitrogen and carbon dioxide for the fine spray dispersion of, for example, liquids or atomizable compositions. The spray device prevents the formation of liquid jet or ion precipitates. Preferably, the spray device contains mineralized waters and controls the pH and the microbial content of the mineralized waters.

10 Claims, 2 Drawing Sheets

SPRAY DEVICE CONTAINING NITROGEN-CARBON DIOXIDE PROPELLANT GAS MIXTURE

BACKGROUND OF THE INVENTION

1. Field of the Invention

The present invention relates a new spray device for the fine spray dispersion of, e.g., liquids such as water including mineral or thermal spring water, comprising a propellent gas mixture.

2. Discussion of the Background

The beneficial physiological and therapeutic properties of mineralized waters, such as mineral and thermal spring waters, have been known for quite some time. Mineralized waters contain beneficial mineral salts and trace elements. Application of mineralized waters as a fine mist to the skin provides the skin with an even distribution of the beneficial mineral salts and trace elements of mineralized waters. In addition, such an application provides an overall feeling of freshness.

Portable personal aerosol containers were developed so that the public could take advantage of the beneficial properties of various waters. For example, as described in F. Clanet, Presse thermale et climatique, 1986, 123, No. 1,: "Le conditionnement des eaux sulfurées en emballages aérosols permettant leur utilisation individuelle" [translation: "The packaging of sulphur waters in aerosol containers would permit their personal use"].

The use of a gag for pressurizing an aerosol container, is well known in the art.

Nitrogen is one gas commonly used to pressurize aerosal containers. However, the pressure of nitrogen gas can cause water soluble ions of high ion content mineralized waters, in particular waters having a high concentration of carbonate or bicarbonate ions, to precipitate. As a result, the chemical composition of the mineralized water is modified which, in turn, can modify the waters' properties and ultimately, the waters' effect on the skin. Furthermore, the ion precipitation increases the risk of blockage of the exit nozzle of the aerosol container which would render the aerosol container inoperable.

Special Medicinal Patent No. 3574 describes the use of carbon dioxide gas in aerosol containers equipped with mechanical propulsion systems. However, when carbon dioxide is used in an aerosol container unequipped with a mechanical propulsion system, several problems result. Instead of a fine spray, which is defined as a cloud of particles having a size of between 50 $\mu$m and 120 $\mu$m, the aerosol container produces water droplets or a liquid jet. Also, liquid leaks form at the atomizer passage of the aerosol container. A spray device that produces such problems is not suitable for marketing.

Also well known in the art is the need to decontaminate the aerosol container once the aerosol container has been pressurized and filled with gas and mineralized water to prevent microbial growth in the water. Decontamination is usually achieved by physical methods, such as heat or ionizing treatments. However, such decontamination methods are very expensive.

Therefore a need still exists for a portable personal aerosol container or spray device which overcomes such problems as ion precipitation, poor spray dispersion and leakage. Furthermore, an alternate and less-expensive decontamination process for a spray device is also needed.

Applicants have surprisingly discovered that a personal aerosol or spray device pressurized by a gas mixture comprising nitrogen and carbon dioxide overcomes these problems and, in addition, provides a liquid, such as water, that is better tolerated by the skin.

SUMMARY OF THE INVENTION

Accordingly, one object of the present invention is to provide a spray device pressurized by a gas mixture comprising nitrogen and carbon dioxide.

Another object of the present invention is to provide a spray device pressurized by a gas mixture comprising nitrogen and carbon dioxide for the application of a liquid or atomizable composition.

Another object of the present invention is to provide a spray device pressurized by a gas mixture comprising nitrogen and carbon dioxide for the application of a liquid or atomizable composition, such as mineralized water, which overcomes the problems associated with previous aerosol containers such as ion precipitates and liquid jet.

Another object of the present invention is to provide a spray device pressurized by a gas mixture comprising nitrogen and carbon dioxide for the application of mineralized water which not only reduces the bacteria content of the mineralized water contained in the spray device, but can also maintain very low levels of bacteria in the water for a lengthy period of time without needing to undergo a physical decontamination process.

Still another object of the present invention is to provide a spray device pressurized by a gas mixture comprising nitrogen and carbon dioxide for the application of mineralized water wherein the gas mixture adjusts the pH of the contained mineralized water close to that of the skin.

Still another object of the present invention is to provide a spray device pressurized by a gas mixture comprising nitrogen and carbon dioxide for the application of a liquid or atomizable composition, such as mineralized water, wherein the liquid or atomizable composition can further comprise cosmetic and/or dermatological adjuvants.

The spray device of the present invention comprises a container, a propellant gas mixture, a valve and a means for atomizing.

DESCRIPTION OF THE PREFERRED EMBODIMENTS

The spray device of the present invention can be used in the application of a liquid or atomizable composition, preferably, of mineralized waters, more preferably, mineral or thermal spring waters. These waters can contain, inter alia, trace elements such as iron (Fe), manganese (Mn), copper (Cu), aluminum (Al) and arsenic (As), and dissolved minerals such as carbonate, bicarbonate ($HCO_3^-$), sulfates ($SO_4^{2-}$), thiosulfates ($S_2O_3^{2-}$), hydrogensulfide ($HS^-$), sodium ($Na^+$), potassium ($K^+$), lithium ($Li^+$), calcium ($Ca^{2+}$), magnesium ($Mg^{2+}$) and strontium ($Sr^{2+}$). It is known that these waters, depending upon the particular mineral and trace element content, can be used for therapeutic purposes such as moisturizing and desensitization of the skin or the treatment of certain dermatoses.

The mineral or thermal spring waters are, preferably, naturally occurring mineral or thermal spring waters or naturally occurring mineral or thermal spring waters enriched with additional dissolvable minerals and/or trace elements or enriched with aqueous solutions prepared from purified water (demineralized or distilled water) enriched with dissolvable minerals and/or trace elements.

Naturally occurring thermal spring or mineral waters for use in the spray device of the present invention are, preferably, water from Vittel, water from the Vichy basin, water from Uriage, water from La Roche Posay, water from La Bourboule, water from Enghien-les-Bains, water from Saint Gervais-les-Bains, water from Néris-les-Bains, water from Allevar-les-Bains, water from Digne, water from Maizières, water from Neyrac-les-Bains, water from Lons-le-Saunier, water from Eaux-Bonnes, water from Rochefort, water from Saint Christau, water from Les Fumades, water from Tercis-les-Bains or water from Avene.

The mineral or thermal spring waters for use in the spray device of the present invention can also be those with relatively high concentration of carbonates or bicarbonates such that precipitate formation is not observed. Mineral or thermal spring waters such as water from Vittel, water from the Vichy basin, water from Uriage, water from La Roche Posay, water from La Bourboule, water from Enghien-les-Bains or water from Les Fumades, contain a total concentration of carbonates or bicarbonates of greater than 360 mg/L, and, upon use, do not exhibit precipitate formation and the disadvantages associated therewith.

The liquid or atomizable composition, preferably mineralized water, contained in the spray device of the present invention can further contain cosmetic and/or dermatological adjuvants such as preservatives, antioxidants, fragrances, UV-screening agents, coloring materials, and hydrophilic or lipophilic active principles. The adjuvants should not effect the integrity of the liquid or atomizable composition, preferably mineralized water, or produce negative side effects once the liquid or atomizable composition, preferably mineralized water, is sprayed onto the skin. The adjuvants are preferably those that can be distributed in the form of a spray or can be atomized. In addition, the adjuvants are preferably those which do not interfere with the working of the spray device, in particular those that do not block the atomizer passage.

Coloring materials or colorants used in the present invention are those well known to those skilled in the art. The colorants can be inorganic or organic colorants or dyestuffs.

Fragrances for use in the present invention are those well-known to one skilled in the art. The fragrances can be natural or synthetic.

The hydrophilic or lipophilic active principles, which are preferably hydrophilic so that they can be dissolved in an aqueous lotion based on mineral water, can treat the skin and can be anti-aging active principles, anti-wrinkle active principles, moisturizers or humectants, depigmenting active principles, active principles for combating free radicals (radical oxygen species), nutritive active principles, protective active principles, restructuring active principles, toning active principles, anti-acne active principles, exfoliating active principles, emollient active principles. The active principles can also treat skin diseases, such as mycones, dermatitides, psoriasis and the like.

Anti-acne, anti-aging, anti-wrinkle, moisturizing or exfoliating active principles are those well-known to one skilled in the art and can, preferably, be α-hydroxy acids such as glycolic, lactic, malic and citric acids and the like.

The active principles are added to the liquid or atomizable composition, preferably, mineralized water in proportions appropriate for its intended purpose. Preferably, 0.01% to 10% by weight of the active principle with respect to the total weight of the composition is added. More preferably, 0.05–5% by weight, more preferably still, 0.1–1% by weight, and even more preferably 0.15–0.5% by weight of the adjuvant is added.

The propellent gas mixture employed in the spray device of the present invention is a mixture comprising nitrogen ($N_2$) and carbon dioxide ($CO_2$). Preferably, the propellent gas mixture consists essentially of $N_2$ and $CO_2$.

Spray tests were conducted with spray devices pressurized by propellent gas mixtures comprising variable percentages by volume of nitrogen and carbon dioxide. The tests indicated that in order to prevent the formation of liquid jet at the end of spraying, the propellent gas mixture, preferably, contained greater than 30% by volume of nitrogen of the total gas volume.

The tests also indicated that in order to prevent the formation of ion precipitates or, when the spray device contains mineralized water, mineral salt precipitates or deposits, the propellent gas mixture preferably contained at least 40% by volume of carbon dioxide of the total gas volume.

The percentage by volume of nitrogen and carbon dioxide of the total gas volume of the propellent gas mixture, preferably, satisfies the relationship (Rel. I):

$$40/60 < \%N_2/\%CO_2 < 60/40$$

and $$\%N_2 + \%CO_2 = 100 \qquad \text{(Rel. I)}$$

More preferably, the percentage by volume of each gas of the total gas volume satisfies the following relationship (Rel. II):

$$\%N_2 = \%CO_2 = 50 \qquad \text{(Rel. II)}$$

but the propellent gas mixture may be composed of 40, 45, 50, 55 or 60% by volume nitrogen with carbon dioxide making up the remainder percentage up to 100%.

The use of carbon dioxide in the propellent gas mixture of the spray device of the present invention can also effect the pH of the liquid or atomizable composition, especially mineral or thermal spring waters, contained in the spray device of the present invention. According to the state of the art, when nitrogen alone is used as the propellent gas, the pH of the contained water at the outlet of the device is between 7 and 8 or neutral to slightly basic. The presence of $CO_2$ in the propellent gas mixture allows $CO_2$ to become dissolved in the contained water and as a result, the pH of the water is lowered or acidified such that the pH is closer to that of the skin, which is between 5 and 6. The pH of the water is usually between 6.0 and 6.9, and, preferably between 6.5 and 6.7. As a result, such water is better tolerated by the skin, especially by sensitive to very sensitive skin.

Furthermore, although carbon dioxide is known for its bacteriostatic properties ("The Inhibition by $CO_2$ of the Growth and Metabolism of Microorganisms", N. M. Dixon, Journal of Applied Bacteriology, 1989, 67, 109–136), a propellent gas mixture of nitrogen and carbon dioxide used in the spray device of the present invention, preferably wherein the nitrogen and carbon dioxide ratio satisfies Rel. I and, more preferably still, satisfies Rel. II, was not expected to reduce the number of germs present in the medium to be sprayed. By having $CO_2$ as a component of the propellent gas mixture, it is possible to obtain a medium of mineral and/or thermal spring water with low levels of contamination of less than or equal to 10 germs per 100 ml and, preferably, of less than or equal to 1 germ per 100 ml, in a few days (methods for counting germs followed as given in the *European Pharmacopoeia,* 2nd Edition, 1983, Vol. I, V.2.1.8) without having to resort to physical decontamination methods.

Different types of means for atomizing or atomizer passages have been tested to optimize the quality of the spray dispersion of a spray device of the present invention as a fine mist. Preferably, an atomizer passage with a nozzle equipped with three vortical channels is used. By using this type of atomizer passage, a propellent gas mixture having a high percentage by volume of carbon dioxide, up to 70% of $CO_2$, can be used in the spray device of the present invention to produce of fine spray or mist without the formation of liquid jet at the end spraying.

The valve of the spray device of the present invention provides a satisfactory feed of the contained medium to the atomizer passage without the risk of blockage. Preferably, a valve which can be used head upwards and head downwards is chosen, in order to avoid loss of propellent gas mixture in the event of improper use of the spray canister. More preferably, a valve which can be used exclusively head upwards is envisaged.

Figure 1A:
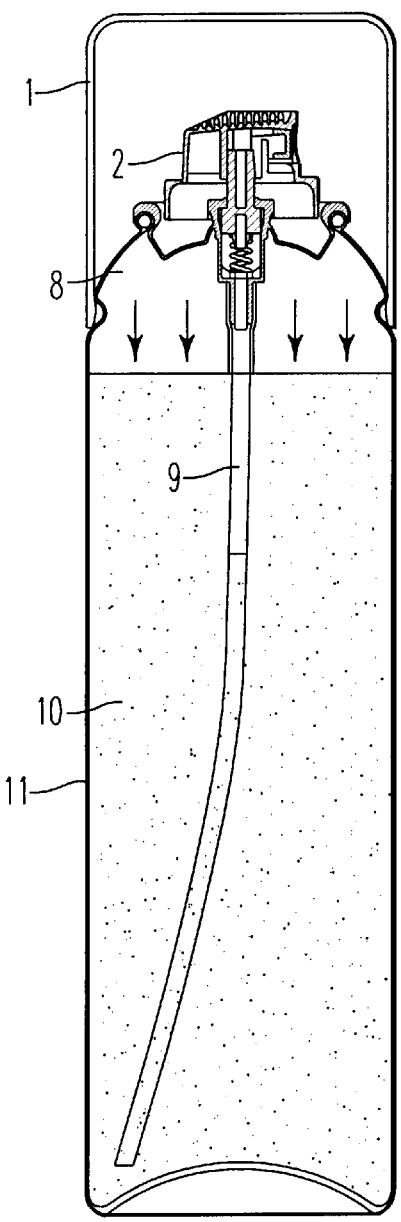
FIGS. 1a and 1b depict a longitudinal cross section of a spray device of the present invention.
Figure 1B:
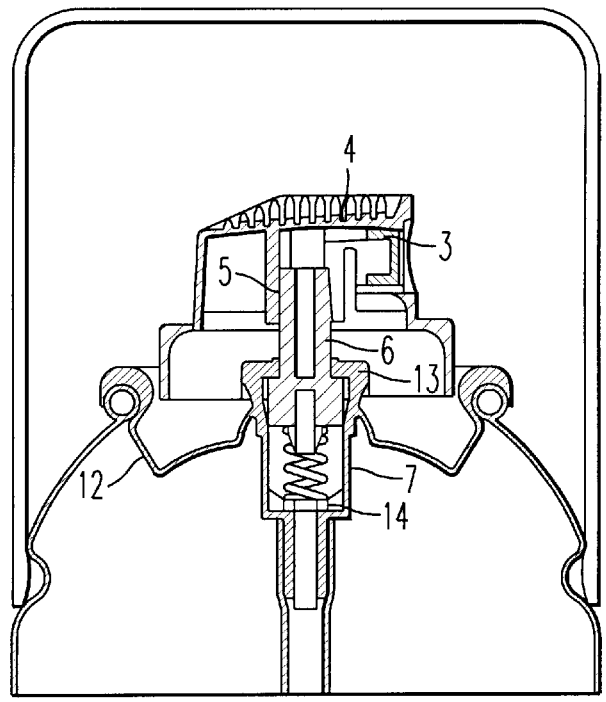

A personal spray device, represented by FIGS. 1a and 1b, comprises a container (11), contained water (10) and a propellent gas mixture (8), a valve and a means for atomizing the water connected to the valve;

the valve is composed of a valve body (7), a dish (12), a rod (6) for actuating the valve and ejecting the water, a seal (13) and a spring (14);

the container (11) is surmounted by a removable cap (1);

the means for atomizing is composed of a diptube (9) attached to the valve body (7) and a push-button (2);

the push-button comprises a coupling (5) which fits onto the rod (6), a distribution channel (4) and a nozzle (3).

Figure 2:
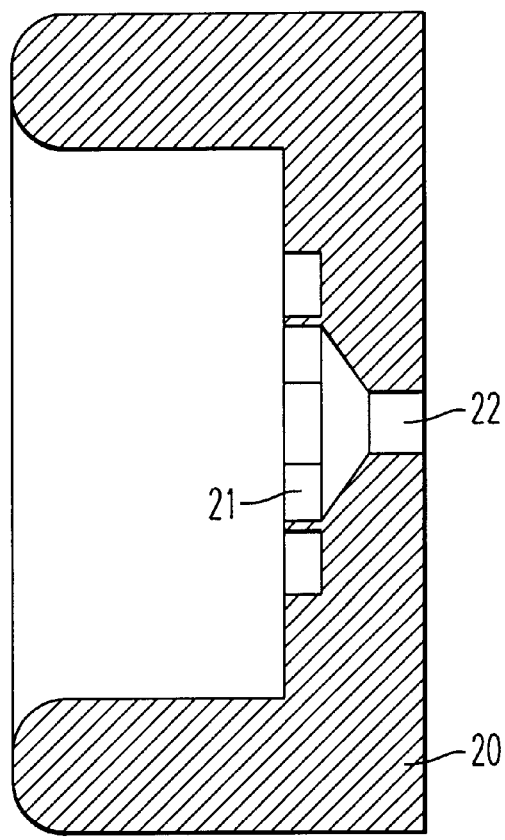
FIG. 2 depicts a longitudinal cross section of an atomizer passage with vortical channels.
Figure 3:
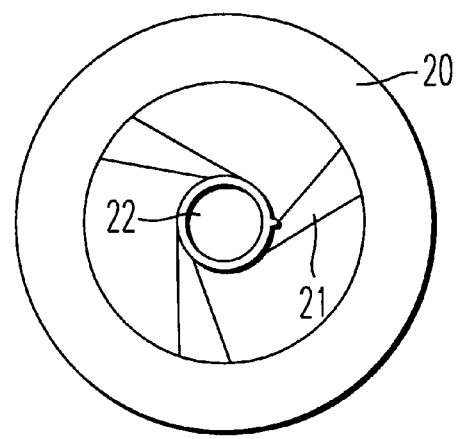
FIG. 3 depicts a transverse cross section of an atomizer passage with vortical channels.

The nozzle (20), which terminates in an orifice (22) and which comprises three vortical channels (21), is illustrated in FIGS. 2 and 3.

Tests

Spray tests were conducted with spray devices of the present invention pressurized by propellant gas mixtures comprising variable percentages by volume of nitrogen and of carbon dioxide. Unless indicated otherwise, the tests are carried out with a spray device of the present invention equipped with an atomizer passage with three vortical channels of a depth of 0.20 mm and fitted with a flat nozzle. The spray tests were conducted using water from the Vichy basin from a spring called Lucas spring.

All percentages are given as percentages by volume. The initial pressure in the device is $6 \times 10^5$ Pas, providing a flow rate of 0.9 g/s for the atomizer passage used. At the end of release, the pressure is $2 \times 10^5$ Pas and the flow rate is 0.5 g/s.

Test 1

The proportion of nitrogen and of carbon dioxide in the propellant gas mixture of the spray device of the present invention was varied and the formation or lack of formation of a jet at the end of release was observed. The results are given a value from 0 to 5 where:

0=no jet
1–2=drops
3–4=low-power jet
5=marked jet formation and are summarized in the table below.

| Gas % $N_2$ | 100 | 80 | 60 | 50 | 40 | 20 | 0 |
|---|---|---|---|---|---|---|---|
| Mixture % $CO_2$ | 0 | 20 | 40 | 50 | 60 | 80 | 100 |
| observations | 0 | 0 | 0 | 0 | 0 | 3 | 5 |

From these tests, it was found that a propellent gas mixture comprising 60% or less of carbon dioxide of the total gas volume did not cause jet formation. 70% carbon dioxide gives useful, but not perfect, results.

Test 2

The effect of carbon dioxide on the pH of the contained mineralized water was evaluated by withdrawing 5 $cm^3$ of water from the outlet of the spray device with an atomizer passage that allows rapid release. For each gas mixture, three water samples were taken and the pH measured. The measurements were then averaged and are summarized in the table below.

| Gas % $N_2$ | 100 | 80 | 60 | 50 | 40 | 20 | 0 |
|---|---|---|---|---|---|---|---|
| Mixture % $CO_2$ | 0 | 20 | 40 | 50 | 60 | 80 | 100 |
| pH | 7.6 | 6.9 | 6.7 | 6.6 | 6.6 | 6.6 | 6.5 |

These tests indicate that the spray device of the present invention pressurized by a propellant gas mixture containing at least 20%, and preferably 40%, by volume of carbon dioxide provides a spray of water having a pH closer to that of the skin.

Test 3

The formation of a calcium carbonate precipitate was evaluated by measuring, by complexometry (unit of measurement=mg/L), the amount of calcium carbonate dissolved in the water at the nozzle outlet, at the beginning of spraying (A) and at the end of spraying or time release (B).

| Gas % $N_2$ | 100 | 80 | 60 | 40 | 0 |
|---|---|---|---|---|---|
| Mixture % $CO_2$ | 0 | 20 | 40 | 60 | 100 |
| A | 53 | 165 | 176 | 170 | 165 |
| B | — | 31 | 161 | 163 | — |

These tests indicate that a gas mixture comprising a higher percentage of nitrogen produces a greater amount of calcium carbonate precipitate. Likewise, when the gas mixture satisfies Rel. (I), no calcium carbonate precipitate is formed.

Test 4

The effect of the gas mixture on bacterial contamination is evaluated. Sterilized physiological water, which would not effect a bacterial population, was contaminated with a given amount of Pseudomonas aeruginosa ATCC19429. The contamination was achieved using calibrated suspensions in order to obtain initial concentrations of (a) $10^5$ germs per 100 ml ($C_{10}^5$) and (b) $10^4$ germs per 100 ml ($C_{10}^4$). These waters were packaged in spray devices according to the invention and pressurized by a gas mixture composed of 50% of nitrogen and of 50% of carbon dioxide (D1). By way of comparison, similarly contaminated waters were packaged (i) in aerosol devices pressurized with nitrogen alone (D2) and, as a control, (ii) in unpressurized aerosol containers (D3). The bacteria content was measured, by filtration, at three different times: at the time of their introduction into the water ($T_0$), after storage for 24 hours ($T_{24h}$) and after storage for seven days ($T_{7d}$) at room temperature (20±2° C.). The results are given as number of germs per 100 ml and summarized in the table below.

|  | $T_0$ | $T_{24h}$ | $T_{7d}$ |
|---|---|---|---|
| D1 $C_{10}^4$ | $1.7 \times 10^4$ | $3 \times 10^2$ | $<5 \times 10^{-1}$ |
| D1 $C_{10}^5$ | $8.5 \times 10^4$ | $1.8 \times 10^2$ | $<5 \times 10^{-1}$ |
| D2 $C_{10}^4$ | $2.2 \times 10^4$ | $1.3 \times 10^4$ | $2.2 \times 10^2$ |
| D2 $C_{10}^5$ | $1.5 \times 10^5$ | $1.3 \times 10^5$ | $1 \times 10^4$ |
| D3 $C_{10}^4$ | $1.7 \times 10^4$ | $1.4 \times 10^4$ | $3.5 \times 10^3$ |
| D3 $C_{10}^5$ | $8.5 \times 10^4$ | $2.4 \times 10^5$ | $4.3 \times 10^4$ |

It is found that the device according to the invention pressurized by a gas mixture of nitrogen and carbon dioxide (D1) reduced the number of germs in the water by at least 4 orders of magnitude, whereas the device pressurized with nitrogen only (D2) and the control device (D3) reduced the bacteria content by a single order of magnitude.

Comparable test results indicate that in devices according to the invention, at room temperature (20±2° C.), the microbial population of a mineral or thermal spring water remained stable for at least nine months.

This application is based on French application 95-12788 filed on Oct. 30, 1995 which is incorporated herein in its entirety by reference.

What is claimed as new and is desired to be secured by Letters Patent of the United States is:

1. A spray device system comprising a container, a propellent gas mixture, a valve, mineralized water, and a means for atomizing said mineralized water, wherein said propellent gas mixture consists essentially of nitrogen and carbon dioxide, wherein the percentage by volume of said nitrogen and said carbon dioxide, of the total gas volume, satisfies the relationship (Rel. I):

$$40/60 < \%N_2/\%CO_2 < 60/40, \text{ and } \%N_2 + \%CO_2 = 100. \quad \text{(Rel. I)}$$

2. The spray device according to claim 1, wherein said mineralized water has a contamination level of less than 10 germs per 100 mL.

3. The spray device according to claim 2, wherein said contamination level is less than or equal to 1 germ per 100 mL.

4. The spray device according to claim 1, wherein the percentage by volume of said nitrogen and said carbon dioxide, of the total gas volume, satisfies the relationship (Rel. II):

$$\%N_2 = \%CO_2 = 50 \quad \text{(Rel. II)}$$

5. The spray device according to claim 1, wherein said mineralized water is a naturally occurring mineral or thermal spring water.

6. The spray device according to claim 1, wherein said mineralized water is selected from the group consisting of water from Vittel, water from the Vichy basin, water from Uriage, water from La Roche Posay, water from La Bourboule, water from Enghien-les-Bains, water from Saint Gervais-les-Bains, water from Néris-les-Bains, water from Allevar-les-Bains, water from Digne, water from Maizières, water from Neyrac-les-Bains, water from Lons-le-Saunier, water from Eaux-Bonnes, water from Rochefort, water from Saint Christau, water from Les Fumades and water from Tercis-les-Bains.

7. The spray device according to claim 1, wherein said mineralized water further comprises at least one adjuvant selected from the group consisting of preservatives, antioxidants, fragrances, screening agents, coloring materials, and hydrophilic or lipophilic active principles.

8. The spray device according to claim 7, wherein said adjuvant is at least one hydrophilic or lipophilic active principle comprising 0.01% to 10% by weight of the total weight.

9. The spray device according to claim 1, wherein said mineralized water is a water which comprises a total concentration of carbonates or of bicarbonates greater than 360 mg/L.

10. The spray device according to claim 1, wherein said means for atomizing water comprises an atomizer passage equipped with a nozzle comprising three vortical channels.

* * * * *